(12) United States Patent
Pierce

(10) Patent No.: US 7,939,729 B2
(45) Date of Patent: May 10, 2011

(54) CELERY CULTIVAR ADS-9

(75) Inventor: Lawrence K. Pierce, Aromas, CA (US)

(73) Assignee: A. Duda & Sons, Inc., Oviedo, FL (US)

( * ) Notice: Subject to any disclaimer, the term of this patent is extended or adjusted under 35 U.S.C. 154(b) by 952 days.

(21) Appl. No.: 11/881,853

(22) Filed: Jul. 30, 2007

(65) Prior Publication Data

US 2008/0016585 A1    Jan. 17, 2008

Related U.S. Application Data

(62) Division of application No. 10/423,295, filed on Apr. 25, 2003, now abandoned.

(51) Int. Cl.
- *A01H 5/00* (2006.01)
- *A01H 5/10* (2006.01)
- *A01H 1/00* (2006.01)
- *A01H 4/00* (2006.01)
- *C12N 15/82* (2006.01)

(52) U.S. Cl. ........ 800/318; 800/260; 800/265; 800/300; 800/301; 800/302; 435/410

(58) Field of Classification Search .................. 800/318, 800/260, 264, 265, 300, 301, 302; 435/410
See application file for complete search history.

(56) References Cited

U.S. PATENT DOCUMENTS

| | | |
|---|---|---|
| 4,753,808 A | 6/1988 | Orr et al. |
| 5,124,505 A | 6/1992 | Orton et al. |
| 5,304,719 A | 4/1994 | Segebart |
| 5,367,109 A | 11/1994 | Segebart |
| 5,523,520 A | 6/1996 | Hunsperger et al. |
| 5,763,755 A | 6/1998 | Carlone |
| 5,850,009 A | 12/1998 | Kevern |

FOREIGN PATENT DOCUMENTS

| | | |
|---|---|---|
| CA | 2523563 | 11/2004 |
| MX | PA/A/2005/011495 | 4/2006 |
| WO | WO 2004/095945 | 4/2004 |
| WO | PCT/US 2004/012523 | 11/2004 |

OTHER PUBLICATIONS

Wolf. 1970. Florida Agricultural Experiment Stations Circular S-208.*
U.S. Appl. No. 10/423,295, filed Nov. 4, 2004, Duda, Darrell L., et al., Corresponding Abandoned Application.
U.S. Appl. No. 10/423,295, filed Nov. 4, 2004, Duda, Darrell L., et al., Restriction Requirement dated Dec. 19, 2005.
U.S. Appl. No. 10/423,295, Nov. 4, 2004, Duda, Darrell L., et al., Response to Restriction Requirement of Dec. 19, 2005 dated Jan. 18, 2006.
U.S. Appl. No. 10/423,295, Nov. 4, 2004, Duda, Darrell L., et al., Office Action dated Apr. 4, 2006.
U.S. Appl. No. 10/423,295, Nov. 4, 2004, Duda, Darrell L., et al., Response to Office Action of Apr. 4, 2006 dated Aug. 3, 2006.
U.S. Appl. No. 10/423,295, Nov. 4, 2004, Duda, Darrell L., et al., Final Office Action dated Oct. 18, 2006.
U.S. Appl. No. 10/423,295, Nov. 4, 2004, Duda, Darrell L., et al., Notice of Appeal dated Apr. 17, 2007.
U.S. Appl. No. 10/423,295, Nov. 4, 2004, Duda, Darrell L., et al., Request for Continued Examination dated Sep. 14, 2007.
U.S. Appl. No. 10/423,295, Nov. 4, 2004, Duda, Darrell L., et al., Office Action dated Nov. 29, 2007.
U.S. Appl. No. 10/423,295, Nov. 4, 2004, Duda, Darrell L., et al., Response to Office Action of Nov. 29, 2007 dated Mar. 28, 2008.
U.S. Appl. No. 10/423,295, Nov. 4, 2004, Duda, Darrell L., et al., Notice Re Non-Compliant or Non-Responsive Amendment dated Jul. 8, 2008.
U.S. Appl. No. 10/423,295, Nov. 4, 2004, Duda, Darrell L., et al., Response to Notice Re Non-Compliant or Non-Responsive Amendment of Jul. 8, 2008 dated Aug. 4, 2008.
U.S. Appl. No. 10/423,295, Nov. 4, 2004, Duda, Darrell L., et al., Final Office Action dated Dec. 5, 2008.
U.S. Appl. No. 12/398,884, filed Jul. 2, 2009, Lawrence K. Pierce, et al., Corresponding Pending Application.
PCT/US 2004/012523, Nov. 11, 2004, WO 2004/095945, Apr. 2004, A. Duda & Sons, Inc., International Search Report dated Feb. 9, 2006.
PCT/US 2004/012523, Nov. 11, 2004, WO 2004/095945, Apr. 2004, A. Duda & Sons, Inc., Written Opinion of ISA dated Oct. 26, 2005.
MX/PA/a/2005/011495, Apr. 2006, A. Duda & Sons, Inc., Official Action dated Jul. 27, 2009.
USDA, ARS, National Genetic Resources Program (Germplasm Resources Information Network—(GRIN). [Online Database] National Germplasm Resources Laboratory, Beltsville, Maryland. Available: http://www.ars-qrin.gov/cgi-bin/napgs/acc/display.pl?1155123 (Oct. 13, 2006).
USDA, ARS, National Genetic Resources Program (Germplasm Resources Information Network—(GRIN). [Online Database] National Germplasm Resources Laboratory, Beltsville, Maryland. Available: hhttp://www.ars-grin.gov/cgi-bin/napgs/acc/display.pl?1155123 (accessed Nov. 13, 2007).
Orton, et al. 1984. Euphytica 33: 471-480.
Quiros, et al. 1993, HortScience 28(4): 351-352.
Stoffella, et al. 1988. Within-row Spacing Effects on Yields of Celery for Processing and Fresh Market. HortScience, Col. 23(6) pp. 988-991.
Browers & Orton, 1986. Biotechnology in Agriculture and Forestry, vol. 2: Crops I, Ed. Y.P.S Bajaj. Springer-Verlag, Berlin, Heidelberg, pp. 405-420.
Eshed, et al, 1996. Less-than-additive epistatic interactions of quantitative trait loci in tomato. Genetics 143:1807-1817.
Kraft, et al, 2000. Linkage disequilibrium and fingerprinting in sugar beet. Theor. Appl. Genet. 101:323-326.
McCarthy, et al., 2001. Commercial celery production in eastern North Carolina. Horticulture Information Leaflet 27, NC State University.

(Continued)

Primary Examiner — Medina A. Ibrahim
Assistant Examiner — Keith O. Robinson
(74) Attorney, Agent, or Firm — Jondle & Associates, P.C.

(57) ABSTRACT

A hollow, individual celery cylinder cut to a length of about one to twelve inches, and having an outside diameter of about 0.1 to 2 inch and an inside diameter of 0.075 to 1.85 inches. The celery cylinder is mild in taste and resistant to rupture upon application of internal vacuum to the cylinder, such that it can be used as a drinking straw. The cylinder can also be stuffed with a foodstuff, to form a novel food product.

21 Claims, No Drawings

OTHER PUBLICATIONS

Quiros, et al., 1987. Use of stem proteins and isozymes for the identification of celery varieties. Plant Cell Reports 6:114-117.

Wolf, E. A. 1970. 'Jun.-Belle', A new early blight resistant celery for late spring harvest in south Florida. Florida Agricultural Experiment Stations Circular S-208.

U.S. Appl. No. 12/818,029, Pierce, Lawrence K., et al., Pending Application—All.

U.S. Appl. No. 12/818,029, Pierce, Lawrence K., et al., Preliminary Amendment dated Jun. 25, 2010.

Booij, R., et al., Cryo-scanning electron microscopy of the apex of celeriac (*Apium graveolens* L. var. *rapaceum* (Mill.) DC.) during initiation of the inflorescence, Scientia Horticulturae (1992), vol. 51, pp. 309-320, Elsevier Science Publishers B.V., Amsterdam.

Booij, R., et al., Flowering in celeriac (*Apium graveolens* L. var. *rapaceum* (Mill.) DC.): effects of photoperiod, Scientia Horticulturae (1994), vol. 58, pp. 271-282, Elsevier Science Publishers B.V.

Booij, R., et al., Effect of photoperiod on flower stalk elongation in celeriac (Apium graveolens L. var. rapaceum (Mill.) Dc.), Scientia Horticulturae (1995), vol. 63, pp. 143-154, Elsevier Science Publishers B.V.

Jenni, S., et al., Early Field Detection of Bolting in Celery, HorTechnology Oct.-Dec. 2005, pp. 843-845.

Lacy, M. L., et al., Department of Botany and Plant Pathology, Fusarium Yellow of Celery in Michigan, May 1985, Extension Bulletin E-1823, Cooperative Extension Service, Michigan State University.

Koike, Steven T., et al., University of California Cooperative Extension Farm Advisors Monterey County, Vegetable Research and Information Center, Publication 7220, Sep. 2003.

Annual Report 1998-99, California Celery Research Advisory Board, Oct. 1, 1998-Sep. 31, 1999.

Yang, X., et al., Identification and classification of celery cultivars with RAPD markers (1993), Theor. App./Ganet 86:205-212.

Thomas, B., Light signals and flowering, Journal of Experimental Botany (2006), vol. 57, No. 13, pp. 3387-3393.

Wittwer, S. H., et al., Gibberellin Effects on Temperature and Photoperiodic Requirements for Flowering of Some Plants, Science, New Series (1957), vol. 3262, pp. 30-31.

Zagory, D., Ph.D., Sanitation Concerns in the Fresh-cut Fruit and Vegetable Industry, University of California, Davis Food Processors Sanitation Workshop (1999), Davis Fresh Technologies, LLC, Davis, California.

Wolf, et al., 1993. 'Florida Slobolt M68: A Spring Celery Cultivar for Florida,' HortScience 28(7):754-755.

\* cited by examiner

US 7,939,729 B2

CELERY CULTIVAR ADS-9

CROSS REFERENCE RELATED TO APPLICATION

This application is a divisional of and claims priority under 35 U.S.C. §119 from U.S. application Ser. No. 10/423,295 filed on Apr. 25, 2003, now abandoned which is incorporated herein in its entirety by reference.

BACKGROUND OF THE INVENTION

The invention relates to celery products including celery straws and food stuffed celery, a class of celery developed to make the products possible including the first celery variety developed for this purpose and the process that especially makes producing these products possible.

Drinking straws are so named because they were originally cut from hollow wheat straw. Over the years, paper and plastics became the preferred material for drinking straws. Nevertheless, it would be advantageous to have an edible and natural material which could be used both for drinking straws, thus forming an edible element of the product being served, and as a holder or container for another foodstuff.

Celery is an edible material known to form hollow cylinders. Celery has been developed into three types with different uses.

Stalk celery is the most prevalent in the United States and Western Europe. This celery has been developed to have large, fairly flat to cupped stems with a solid, crisp interior. Frequently, the top-most leaves and roots are removed before sale and consumption. Stems with entire leaves are available for consumption in the center of the plant, called the heart, and these stems are sold like outer stems. Breeding has been used to make stalk celery greener, of milder flavor and generally more solid and crisp.

Root celery is often grown in cooler climates. Unlike stem celery, root celery has been developed to have an enlarged hypocotyl or root bulb often weighing one to two pounds. The stems, leaves and small roots are removed from this swollen root ball, which is used much like the potato, and which may be fried or mashed, or used in stews and soups. The stems and leaves are bitterer than those of stem celery. The stems may be hollow, solid, or in between.

Leaf celery or smallage has been developed primarily for leaf and seed production. Often grown in Mediterranean climates, leaf celery more closely resembles celery's wild ancestors. The stems are small and vary from solid to hollow and the leaves are fairly small and are generally bitter. This type is often used for its medicinal properties and spice.

SUMMARY OF THE INVENTION

It is therefore the object of the invention to provide a new type of celery that will have uses that are entirely different from the traditional stem celery, root celery and leaf celery types. This new type of celery is hollow-stem celery, which combines attributes from stem celery, with those of root or leaf celery. Though each of these types of celery has been identified by its own subspecies designation, they are fully sexually and genetically compatible with one another.

Thus, the genetic traits from each may be combined to create a new type/category of celery with different purposes and uses not considered before now. Hollow-stem celery combines the sweet/mild flavor, less fibrous/tough/chewy texture, and longer petiole length found in solid stemmed, stem celery (*Apium graveolens* L. var *dulce*) with the small diameter (6.25 to 9.38 mm) hollow petiole that is found in the fibrous and bitter stemmed, root celery (*Apium graveolens* L. var *rapaceum*) and leaf celery (*Apium graveolens* L. var. *secalinum*) types.

It is a further object of the invention to develop a new set of products from this new type/category of celery. Different varieties of hollow stem celery have been developed that have different characteristics like stem diameter (6.25 to 37.5 mm plus) to meet the specific criteria for each of the current/future products.

One such new product is the celery straw. A celery straw is a natural straw that can be used for the consumption of beverages, and which is advantageous in that it is capable of enhancing the flavor of the beverage, can be consumed after or during the consumption of the beverage and is totally biodegradable.

A second product is raw, stuffed hollow-stem celery. For years, celery has been associated with other food products like peanut butter, cream cheese, cheese and dressings such as blue cheese and ranch. Generally these food products are spread over the cupped side of a raw stick of stem celery, or the celery stick is used as a scoop and dipped into a bowl containing the product. The result is generally messy and does not lend itself to consumption as a packaged, ready to eat, on the go food.

According to the invention, medium to large diameter (approximately 9.38 to 18.75 mm diameter) hollow-stem celery varieties can be utilized to create stuffed celery products which will be ready to eat and free of the mess because the food product will be disposed on the inside of the stem. The hollow-stem celery can be cut to various lengths depending on the product or market and then stuffed with an unlimited number of potential stuffing products. These may then be classified as a ready to eat, on the go food.

A third product is cooked, stuffed hollow-stem celery. This product may be produced in various forms. For example, the hollow stem celery may be stuffed with a food product and then baked, battered and deep-fried, grilled, etc. Products may be precooked and frozen, while others may be stuffed and frozen in the raw state for cooking later and still others may be stuffed in the raw state and sold fresh for cooking.

DETAILED DESCRIPTION OF THE INVENTION

Characteristics of the Celery Plant

A new type of hollow-stem celery has been produced according to the invention, under the designation ADS-9, which combines the mild stem flavor from stem celery with the hollow stem of a leaf celery line from China.

One plant from an accession identified as 'China B' possessing typical leaf celery characteristics was cross pollinated with a single plant from the stem celery variety Hill's Special (PVP 9500019). China B was selected out of three different unnamed Chinese leaf celery types because it had the best dark green color. Hill's Special was selected as the alternate parent because it possessed excellent bolting tolerance, and large thick, fairly stringless petioles with good mild flavor. At the time that the original crosses were made, it was considered critical that the stem celery parent have very strong bolting tolerance, as most leaf celery lines have very little bolting tolerance since they are developed to produce seed with very little vernalization. It is not desirable to have hollow-stem celery with low vernalization requirements because it would tend to bolt or go to flower in the middle of the late winter, spring and early summer production times in California rendering it unfit for harvest. At the time of the initial crosses, Hill's Special was in its initial development stage.

Hill's Special is currently the most bolting resistant variety in existence and considered bolting resistant under California production conditions. It is protected under the Plant Variety Protection designation PVP 950019.

Plants from both parents were selected from trials grown in Oxnard, Calif. where the traits were observed and noted (Table 1; ADS-9 has been included for comparison.) Cross pollination was accomplished by the method described by Shig Homna (Honma, S., 1959, A method for celery hybridization. Proceedings of the American Society of Horticultural Science 73, 345-348). The resultant seed from both reciprocal crosses (each parent behaving as female and male) were then planted in a greenhouse nursery in planting trays with 1 inch square plugs filled with a peat type medium. Ten plants from each of the reciprocal crosses were then transplanted to larger 5 gallon pots after approximately 9 weeks in a similar peat type mix. These plants were allowed to become considerable larger and after an additional 10 weeks were then vernalized by exposure to temperatures of approximately 45° F. for and additional 4 weeks. These plants were transplanted to a field where they were placed into two mesh fabric cages; each reciprocal cross having its own cage. These cages were designed to allow wind penetration so that the plants could be wind pollinated and to hold flies that were placed with in the cage to assist in pollination. Seed was harvested and bulked from the 10 plants in each of the cages ($2^{nd}$ filial generation). Seeds from each cage were then planted in trays filled with a peat mix medium at a transplant nursery with care being taken to keep the particular reciprocal cross separate. After approximately 9 weeks these transplants were then transplanted into a commercial celery field. The particular lines were each evaluated and the plants with the most desirable characteristics selected. Several different breeding protocols were utilized in subsequent generations to break the association of bitterness with hollow stem and to gain larger, less stringy hollow stem characteristics more similar to Hill's Special.

Table 1 shows a comparison between ADS-9 and its parents, Hill's Special and China B for various defining phenotypic characteristics and measurements. These measurements were based primarily on data collected at Salinas, California Research Station and Oxnard, Calif. field plots.

TABLE 1

| Variety Description Information | | | |
|---|---|---|---|
| | Hill's Special | China B | ADS-9 |
| Overall Plant Height (cm) | 63.4 | 60.1 | 99.0 |
| Petiole Length to Joint (cm) | 25.2 | 22.1 | 57.7 |
| Petiole Width to Midpoint (mm) | 26.1 | 6.7 | 11.6 |
| Petiole thickness at Midpoint (mm) | 8.9 | 6.7 | 9.3 |
| Number of petioles greater than 40 cm | 9.6 | 7.6 | 13.7 |
| Number of petioles less than 40 cm | 9.0 | 21.3 | 4.4 |
| Petiole Color (RHS*) | 5 gy 6/6 | 5 gy 3/4 | 5 gy 4/6 |
| Stem type | Solid | Hollow | Hollow |
| Variety that flavor most resembles | Tall Utah 52-75 | PI 179171 | Junebelle |

*Royal Horticulture Society of England botanical color chart for quantifying color numerically ADS-9 has other significant advantages. Unlike most stem celery varieties which are only capable of being grown in California in plant populations of approximately 47,000 plants per acre, ADS-9 is capable of being produced at 65,000 plants per acre. This provides significant yield advantage while the plant competition minimizes the variation of stem diameters from the outside to the center of the plant. Table 2 represents the straw yield from three different test productions that were grown in Salinas, Calif. (Test Production #1) and Oxnard, Calif. (Test Productions #2 and 3) for one acre of ADS-9; a straw length of 7 inches was utilized.

TABLE 2

| Finished yield for ADS-9 from three test productions. Yield is calculated as the number of 7 inch straws per acre. | | | |
|---|---|---|---|
| | Average number of 7 inch straws per plant | Range of number of straws per plant | Yield in total straws per acre |
| Test production #1 | 30.8 | 25 to 42 | 2,002,000 |
| Test production #2 | 26.9 | 18 to 37 | 1,748,500 |
| Test production #3 | 26.7 | 18 to 33 | 1,735,500 |

Subsequently, similar crosses have been made between numerous stem celery varieties and different varieties of root and leaf celery for the development of larger diameter hollowstem celery varieties. This invention, therefore, is not limited to variety ADS-9 and products made therefrom, but encompasses products made from other hollow-stem celery varieties which have mild flavour, which are sufficiently rigid, and which are bred to achieve desirable characteristics, for example, dimensions, color, flavor, disease resistance, etc.

Because celery has eleven chromosomes with many genes on each chromosome and two or more alleles possible for each gene, it is possible that an almost infinite number of possible combinations and resultant progeny can occur from a cross between the types. Thus, a very defined and intentional approach was developed in order to achieve the specific characteristics desired for a hollow class of celery. Because this class of celery did not previously exist and had no conceived market value, no one has put forth the considerable effort required to develop the new class of celery.

Once the basic gene linkages with undesirable characteristics are broken and numerous desirable traits are combined into an adequate type, breeding for different refined characteristics becomes slightly easier.

Breeding of celery is a slow and time consuming process. Celery is a biennial crop requiring two years in order to go to flower and produce seed.

The biennial nature of celery occurs because celery requires a vernalization period in order to convert from vegetative growth into a reproduction mode. Vernalization varies with different varieties of celery but always requires a plant of a minimum maturity in order to be responsive to the cooler temperatures. There is also evidence that celery is daylight sensitive and that shorter days also help promote the transition into reproduction.

It is also difficult to achieve controlled cross pollination in celery because celery is an umbelliferous species and exhibits protandry.

Celery produces hundreds of clusters of very small flowers that all mature at different times. Most of these flowers are arranged in smaller umbellules which are smaller umbel type clusters. Within each umbellule the outer flowers in the cluster mature or open first and then they develop and open, sequentially, towards the center of the cluster over several days.

There is also a pattern of outer umbellules maturing first and then progressing inward. Controlling pollination or cross pollination is further complicated in celery because each flower is protandrous meaning that the female portion of the flower is mature and receptive 4 to 6 days after the maturity of the male portion and subsequent shed of pollen.

However, because of the great diversity of flower maturities there is almost always pollen present within an umbel to confuse controlled pollination. Thus, controlled pollination is difficult, tedious and very labor intensive. It is also very difficult to ensure accurate and proper controlled pollination.

Once the initial crosses are achieved, there are several methods or development protocols that can be followed in order to identify and ensure that the traits desired are brought together. These include but are not limited to selfing or inbreeding, additional crossing and backcrossing.

With inbreeding, progeny from the crosses are grown out and plants that have some of the traits that are desirable are self pollinated (pollen from itself is utilized to pollinate itself). In this manner the traits that are desired are fixed (locked together). However, because so many traits have to be combined, thousands of plants have to be evaluated and because of the thousands of potential allelic combinations the odds of finding the one plant expressing all of the characteristics desired is limited. This is especially true since many traits which reside closely on the same chromosome frequently remain linked with one another. In many instances multiple genes may act together to create a particular trait so simultaneous alterations are required for each particular gene.

Thus, other techniques such as backcrossing are utilized in order to introduce a known character from a parent or contributor to an existing line, i.e. if a line is currently hollow but bitter, a sweet celery parent is selected and crossed with the hollow type.

Progeny that have improved flavor but retain the hollowness are kept. These are then crossed with the sweet parent again in order to add more of the mild alleles to the hollow-stem line. This is repeated for several generations until the flavor resembles the mild type, with retention of the character for hollowness, a procedure which may take 7 or more generations or 14 plus years.

Another possibility is that the parents originally crossed did not have all of the proper characteristics or alleles represented so additional crosses are made to other parents to contribute still other traits.

Other methods are also available, and several in combination facilitated the development of hollow-stem celery and in particular ADS-9.

Application of Hollow-Stem Celery to Celery straws and Food Stuffed Hollow-Stem Celery The development of a new class of celery, hollow-stem, was initiated in order to provide a product that would be functional as celery straws and food stuffed hollow celery products. Until a suitable hollow-stem celery variety was developed, no final product development could occur for straws or stuffed products.

The proposed new products and any future products that are developed from, or utilize hollow-stem celery as a primary ingredient may differ in their specifications of the hollow-stem celery that is required in the product/process.

It is possible that in a single product, the specifications may be different for different customers, or end uses/users. Thus, different varieties may be refined within the class of hollow-stem celery to meet the specific criteria, or specifications for the individual product.

For example, some of the products or customers require hollow-stems with larger diameters and others require hollow-stems with smaller diameters.

A single celery variety will not, therefore, be sufficient to meet all of these criteria, and the breeding effort will not stop with the development of the new and distinct celery ADS-9 with in the new celery class (hollow-stem celery). However, the initial concept for the development of the new class of celery, hollow-stem, which is more palatable (mild flavored and less fibrous) remains a constant for each.

Flavor in celery is a complex of several compounds which together create a flavor profile for a variety. Several different classes of compounds act together at varying levels to create a flavor that is not only unique for celery, but fairly unique to the individual variety. Some of these compound groups include, but are not limited to sugars, carotenoids, linear furanocoumarins, etc.

There are three primary types of sugar that maybe actively involved in the flavor profile for celery and each has its own characteristic contribution to the overall sweetness of the celery. For instance fructose which is commonly found in celery has a sweetness equivalent of 140 while glucose has a sweetness rating of 70-80 and sucrose has a rating of 100. Each variety may have a different ratio each of these sugars, hence a different sweetness contribution.

Similarly, there are several different carotenoids and furanocoumarins that may contribute to the overall flavour complex in celery with each making a slightly different contribution. Carotenoids are frequently associated with the carrot flavor of carrots and similarly have a little contribution to the overall flavor of celery.

However, the most prominent set of compounds that have the single most dramatic effect on the flavor of celery belong to a class called the linear furanocoumarins to which three particular compounds in celery belong, psoralen, bergapten and xanthotoxin. This set of compounds is essentially responsible for the strong, slightly bitter flavor associated to celery. In fact higher levels of furanocoumarin type compounds frequently mask the flavor contributed by the sugars and carotenoids in celery. These same compounds are responsible for natural plant defense responses in celery and become elevated when celery is diseased or grown under stressful conditions. Furanocoumarins are also responsible for the phenomenum called celery rash which may occasionally affect handlers of celery. When present on a person's skin, furanocoumarins may be photo-activated by light and cause a rash similar to poison ivy in susceptible persons. The levels of furanocoumarins are generally highest in the wild species of celery, celeriacs (root celery) and leaf celery.

This flavor complex can vary for a variety from one production condition to another, especially under conditions that vary for the presence of disease and/or stress. However, the relationship of flavor between varieties remains fairly constant with respect to one another under these varying conditions. Therefore a table rating the overall flavor of different varieties in relationship to one another is an excellent means for comparing the overall flavor for an individual variety.

Following is a table that rates the flavor for several varieties. They range from rating 1 (sweet) to 10 (bitter). Most stem varieties are in a range from 3 to 5 which is generally considered mild flavor. Celery leaf and celery root varieties are classified 9 and 10 (bitter). The inventor has chosen to develop hollow-stem celery varieties that are rated 5 or less (ADS-9 is 5).

TABLE 3

Flavor Ratings (1-10)

Sweet ◄─────────────────────────────────────► Bitter

| 1 | 2 | 3 | 4 | 5 | 6 | 7 | 8 | 9 | 10 |
|---|---|---|---|---|---|---|---|---|----|
| ADS-1 | | Tall Utah 52-75 | Florida Snowbolt | ADS-9 | Giant Red | | | Diamonte | Celeriac* |
| | | Conquistador | Florida 683 'K' Strain | Junebelle | | | | | China B |
| | | Sonora | Tall Utah 52-70 'R' Strain | | | | | | PI 179171** |
| | | Floribelle | | | | | | | PI 175591** |
| | | | | | | | | | Edible Ornamental |
| | | | | | | | | | Root celery* |

*These are commercial variety names as opposed to the general type or classification of celery referred to as celeriac or root celery.
**Lines that are prefaced with PI are items that have been donated, found, or otherwise collected as wild types, finished varieties, old land races, etc. and are now part of the USDA-ARS Plant Germplasm Resource system. These lines are entered into the USDA-ARS system and assigned Plant Introduction numbers (PI).

The fibrous character in celery and its different forms is generally a result of the vascular bundles which provide transport through the stem. These vascular bundles vary in their placement within the stem, their diameter and the quantity. The varieties or types of celery that are classified as less fibrous or stringy generally have fewer, but larger vascular bundles that are located deeper with in the stem (further below the surface). Varieties that are more fibrous have more bundles that are smaller and located nearer the surface of the stem. Since vascular bundles are physiological requirement there is no variety that is considered to be truly non-fibrous (0 fibers).

The difficulty with hollow-stem celery is that these vascular bundles are all located fairly close to the surface because the stem is not as thick as stem celery but actually hollow. Therefore, hollow-stem celery has now been developed according to the invention having fewer and larger vascular bundles often associated with the less fibrous stem varieties, but because these bundles are nearer the surface, they still give a sensation of being more fibrous than many stem varieties. However when compared with root celery and leaf celery types they are still less fibrous.

The level of fibrousness in celery, like flavor, is often affected by environmental conditions with different levels of stress, drought, maturity, fertility and disease having an effect. However, the relationship of texture between varieties remains fairly constant with respect to one another under these varying conditions. Therefore a table rating the overall texture of different varieties in relationship to one another is an excellent means for comparing the overall fibrousness for an individual variety.

Following is a table that rates the texture for several varieties. They range from rating 1 (non-fibrous) to 10 (fibrous). Most stem varieties range from 2 to 6 which is generally considered less fibrous. Celery leaf and celery root varieties are generally classified as 9 to 10 (fibrous). Hollow-stem celery varieties are rated 6 to 7 (ADS-9 is 6).

TABLE 4

Texture Rating (1-10)

Non-Fibrous ◄─────────────────────────────────────► Fibrous

| 1 | 2 | 3 | 4 | 5 | 6 | 7 | 8 | 9 | 10 |
|---|---|---|---|---|---|---|---|---|----|
| ADS-1 | Floribelle | Tall Utah 52-75 | Florida 683 'K' Strain | Junebelle | Giant Red | | Edible Ornamental | | Celeriac* |
| | Hill's Special | Conquistador | Tall Utah 52-70 'R' Strain | Florida Snowbolt | Pacifica | | | | China B |
| | ADS-8 | Sonora | | | ADS-9 | | | | Diamonte |
| | | | | | | | | | PI 175591** |
| | | | | | | | | | PI 179171** |

*This is a commercial variety names as opposed to the general type or classification of celery referred to as celeriac or root celery.
**Lines that are prefaced with PI are items that have been donated, found, or otherwise collected as wild types, finished varieties, old land races, etc. and are now part of the USDA-ARS Plant Germplasm Resource system. These lines are entered into the USDA-ARS system and assigned Plant Introduction numbers (PI).

The celery straw has advantages for beverages like tomato juicer, Bloody Mary drinks and beer because the straw adds natural celery flavor to the beverage as they are consumed through the straw; the acids of the tomato, vegetable or fruit and the alcohol extract some of the natural celery flavor as the beverage passes through the straw. This celery flavor acts to enhance the overall beverage character. The natural celery straw can also be consumed once the drink is completed. If it is not consumed the natural straw has an advantage of being totally biodegradable.

The specifications of the hollow-stem celery required for the straw may vary, but it will generally be, but not be limited to, 6.25 to 12.5 mm (approx. 0.25-0.50 inches) in diameter; this is primarily due the difficulty in drinking a beverage comfortably through a very large straw.

The length of the straw itself may also vary depending on the size of the glass used or the customers' individual preferences. Standard plastic straws are generally 7 to 8 inches, but can be found up to 11 or 12 inches. Celery straws can be produced and cut to meet the same measurements.

Some drinks, especially those that are more viscous may require larger diameter straws in order to get the beverage to flow. Others like Martinis may require a straw more similar to a swizzle stick, having a shorter length, i.e. 4-6 inches, with a diameter of approximately 3.13 mm (0.125 inches).

The invention of food stuffed hollow celery may take several forms. Stuffed, raw celery products may require hollow-stem celery with different dimensions depending on the specifications, product format or presentation.

Stuffed, raw celery is hollow-stem celery that is cut to a particular length and stuffed or filled with a product to enhance the celery. These stuffing or filling products can include but not be limited to peanut butter, cream cheese, cheese and dressings (blue cheese, ranch, etc.), chocolate, candy fillings, fruits, etc.

The fillings may have to be specially formulated to be injected into the hollow-stem celery, but can be of essentially any flavor. Currently most of these food products are spread over the surface of the raw celery stick and tend to be messy. Stuffed celery will be less messy and may be classified as ready to eat on the go food.

Raw, stuffed celery is anticipated to use primarily, but not be limited to, medium to large diameter (approximately 9.38 to 18.75 mm, approx. 0.375-0.75 inches, in diameter) hollow-stem celery. Again, different customers may have different specifications (length, diameter, thickness, color, etc.) for their particular use.

Some of these specifications may change as the products develop or as new uses evolve so corresponding refinements may have to be made to either the hollow-stem celery varieties or the process in which they are cut and prepared.

Cooked stuffed hollow-stem celery may be similar to raw stuffed hollow-stem celery except it is cooked in its final form.

The product may take various forms including, but not limited to, being filled with a cheese type product and baked like a manicotti, or filled and cooked like an enchilada, or stuffed, battered and deep fried like a jalapeno popper.

Some of these products may be precooked and frozen others may be stuffed and frozen in the raw state for cooking later and still others may be stuffed in the raw state and sold fresh for cooking.

This type of product is likely to utilize larger diameter hollow stem celery varieties (12.5 to 37.5 mm, approx. 0.50-1.5 inches, in diameter) but the specifications may vary by product or customer preference.

Preparation of Celery Straws and Food Stuffed Hollow-Stem Celery

In the preparation of a product for the marketplace, raw hollow-stem celery is harvested by hand or machine in the field similar to standard stem celery and placed in bins, totes or cartons and cooled. Cooling will usually be performed by utilizing hydro-vac cooling, hydro cooling or forced aircooling methods typical of most raw vegetables, but other methods may be used.

The initial processing steps may include cleaning steps often used for raw vegetables to assure cleanliness and food safety.

Once the hollow stem celery is cooled, the cool chain will be maintained within the range of 33 to 40° F. unless the specific product or process requires a break in that chain.

The celery may either be cut by hand or mechanical means such as a saw or knife. It may also be cut with a water knife or similar type advancements in cutting technology.

The invention celery straw, a novel and natural straw that can be utilized for the consumption of beverages, is the result of cutting the petioles of hollow-stem celery in a manner that maintains the integrity of the hollow stem. Maintenance of the integrity of the stem is especially critical because holes or cracks in the product/straw will result in an unusable product.

The water knife/water jet cutter is a special technology which has been adopted specially for cutting hollow-stem celery. Due to the hollow nature of the product, conventional knives and saws have a greater opportunity to collapse the straw at the point of impact, thus causing the straw to rupture, split or crack. Once a straw is damaged it is difficult or even impossible to consume a beverage through it.

However, the water knife cuts by a very high pressure stream of water and air (over 37,000 psi) being passed through a very small orifice or nozzle (approximately, but not limited to, 0.007 mm in diameter). The hollow-stem celery passing through this high pressure stream of air and water is cut with no risk of straw collapse, because no physical pressure is applied to the hollow-stem celery.

Water is first run through a prechiller which drops the temperature to between 34 and 36° F. The water is then run into an intensifier where it is run through a filtration system to remove impurities. The intensifier then compresses water and air independently. A stream of water is then injected into the air such that the air acts as the carrier and the water as the abrasive. This mixture passes through a set of cutting nozzles (>37,000 psi) that have an orifice between 0.003 and 0.010 mm in diameter.

Several water jet nozzles are placed in series at intervals that match the length of the celery straws that are desired. The whole hollow-stem celery stalk is then passed through these nozzles or knives on a conveyor. As the celery stalk passes though the pressurized water emanating from each nozzle it is cut. The length of the cuts will depend on the specific product or the requirements of the consumer.

Additional cleaning steps typical of raw, semi-processed and processed vegetables may be utilized to assure cleanliness and food safety. These steps may include chlorine or other cleansing/sterilizers in rinse water applied via a drenching or water bath system. Typical solutions include chlorine and water at a concentration of approximately 750 ppm or cleansing/sterilizers at their suggested use rates. Other technologies may be utilized as appropriate or acceptable.

All products should be handled from this step forward in an aseptic environment following general HACCP procedures in order to ensure food safety.

The cut and cleaned hollow stem celery is sorted or graded by size and quality based on standards established for the specific products, uses or customer requirements. The celery will be run through a metal detector following processing or prior to or following packaging to ensure that no metal has contaminated the product.

Celery straws will be packaged and sealed in various container types according to the customer's requirements. The cool chain remains unbroken for this product, as it is sold as a perishable product.

Celery straws may be handled in a slightly dehydrated (wilted or limber) state and then rehydrated by the consumer by placing in a container with clean water for several minutes. The consumer may trim the ends with a knife to improve freshness, appearance, or adjust the length.

Stuffed celery straws, raw or cooked, maybe stuffed with an injection system specifically modified to match the diameter of the hollow stem celery and the consistency of the food product being injected.

Depending on the particular food product being injected, another cooling procedure may be required to re-establish an appropriate temperature. This cooling procedure, if required, may take place prior or just following packaging in customer specified packaging. The cold chain must be maintained throughout shipment and delivery to the customer.

Each type of cooked, stuffed product may have an entirely different treatment or preparation process.

EXAMPLE

Hollow stem celery is field harvested in bulk bins (40"×48"×48") and delivered to a processing plant. The bins are placed in a Hydro-Vac tube where sanitized spray water is added and then a vacuum is drawn to bring the product temperature to approximately 34° F.

The celery is placed on a conveyor belt, oriented so that it can pass through a water knife to cut off the butt or base of the plant and the top or leaves. The water knives are set to obtain the length desired for the straws or stuffed product. The celery butt and tops fall off the belt and the cut sections are conveyed through a chilled, disinfecting water shower.

These sections then pass through an air shower to remove excessive moisture, and the conveyer belt continues to carry the sections to a sorting station where the product is graded manually to meet the standards for the product and customer.

If the product is a straw, the straws are then carried via a conveyor to packing stations where they are manually packed in the appropriate packaging.

If packed in poly sealed bags the packages are run through a sealer where they are date stamped with a "use by" date specific to the specific product. They continue through a metal detection device and are then placed in cartons and sealed for shipment.

If the product is a stuffed hollow stem celery product, the larger hollow stem celery variety sections are carried via conveyor from the sorting and grading conveyor to a filling/stuffing station. Here the straws are filled using a stainless food grade injector and then conveyed to a packing station where they are packaged in appropriate packaging.

The sealer is again used for sealing, a metal detector is used to check for contamination and a boxing station places the containers into cartons for shipment.

If the stuffed hollow stem celery is to be cooked the process breaks just after the filling station, depending on the specific product.

Deposit Information

A deposit of the A. Duda & Sons, Inc. proprietary inbred celery cultivar ADS-9 disclosed above and recited in the appended claims has been made with the American Type Culture Collection (ATCC), 10801 University Boulevard, Manassas, Va. 20110. The date of deposit was Jun. 17, 2004. The deposit of 2,500 seeds was taken from the same deposit maintained by A. Duda & Sons, Inc. since prior to the filing date of this application. All restrictions upon availability to the public will be irrevocably removed upon granting of the patent, and the deposit is intended to meet all of the requirements of 37 C.F.R. §§ 1.801-1.809. The ATCC accession number is PTA-6083. The deposit will be maintained in the depository for a period of 30 years, or 5 years after the last request, or for the effective life of the patent, whichever is longer, and will be replaced as necessary during that period.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to included all such modifications, permutations, additions, and sub-combinations as are within their true spirit and scope.

What is claimed is:

1. A seed of celery cultivar ADS-9, representative sample of seed of said cultivar was deposited under ATCC Accession No. PTA-6083.

2. A celery plant, or a part thereof, produced by growing the seed of claim 1.

3. A tissue culture produced from protoplasts or cells from the plant of claim 2, wherein said cells or protoplasts of the tissue culture are produced from a plant part selected from the group consisting of callus, meristematic cell, leaf, pollen, embryo, root, root tip, anther, pistil, flower, seed, petiole and sucker.

4. A celery plant regenerated from the tissue culture of claim 3, wherein the plant has all of the morphological and physiological characteristics of cultivar ADS-9.

5. A method of producing a celery seed comprising crossing two celery plants and harvesting the resultant celery seeds, wherein at least one celery plant is the celery plant of claim 2.

6. A celery seed produced by the method of claim 5.

7. A celery plant, or a part thereof, produced by growing said seed of claim 6.

8. A method of producing an herbicide resistant celery plant wherein the method comprises transforming the celery plant of claim 2 with a transgene wherein the transgene confers resistance to an herbicide selected from the group consisting of imidazolinone, sulfonylurea, glyphosate, glufosinate, phenoxy proponic acid, L-phosphinothricin, triazine and benzonitrile.

9. An herbicide resistant celery plant produced by the method of claim 8.

10. A method of producing a pest or insect resistant celery plant wherein the method comprises transforming the celery plant of claim 2 with a transgene that confers pest or insect resistance.

11. A pest or insect resistant celery plant produced by the method of claim 10.

12. The celery plant of claim 11, wherein the transgene encodes a *Bacillus thuringiensis* endotoxin.

13. A method of producing a disease resistant celery plant comprising transforming the celery plant of claim 2 with a transgene that confers disease resistance.

14. A disease resistant celery plant produced by the method of claim 13.

15. A method of producing a celery plant with modified fatty acid metabolism or modified carbohydrate metabolism comprising transforming the celery plant of claim 2 with a transgene encoding a protein selected from the group consisting of fructosyltransferase, levansucrase, α-amylase, invertase and starch branching enzyme or encoding an antisense of stearyl-ACP desaturase.

16. A celery plant having modified fatty acid metabolism or modified carbohydrate metabolism produced by the method of claim 15.

17. A method of introducing a desired trait into celery cultivar ADS-9 comprising:
 (a) crossing ADS-9 plants grown from ADS-9 seed, wherein a representative sample of seed was deposited under ATCC Accession No. PTA-6083, with plants of another celery cultivar that comprise a desired trait to produce progeny plants, wherein the desired trait is selected from the group consisting of male sterility, herbicide resistance, insect resistance, disease resistance, modified fatty acid metabolism, modified carbohydrate metabolism, and resistance to bacterial disease, fungal disease or viral disease;
(b) selecting one or more progeny plants that have the desired trait to produce selected progeny plants;
(c) crossing the selected progeny plants with ADS-9 plants to produce backcross progeny plants;
(d) selecting for backcross progeny plants that have the desired trait and the physiological and morphological characteristics of celery cultivar ADS-9 listed in Table 1 to produce selected backcross progeny plants; and
(e) repeating steps (c) and (d) three or more times in succession to produce selected fourth or higher backcross progeny plants that comprise the desired trait and the physiological and morphological characteristics of celery cultivar ADS-9 listed in Table 1.

18. A celery plant produced by the method of claim 17, wherein the plant has the desired trait.

19. The celery plant of claim 18, wherein the desired trait is herbicide resistance and the resistance is conferred to an herbicide selected from the group consisting of imidazolinone, sulfonylurea, glyphosate, glufosinate, phenoxy proprionic acid, L-phosphinothricin, triazine and benzonitrile.

20. The celery plant of claim 18, wherein the desired trait is insect resistance and the insect resistance is conferred by a transgene encoding a *Bacillus thuringiensis* endotoxin.

21. The celery plant of claim 18, wherein the desired trait is male sterility and the trait is conferred by a cytoplasmic nucleic acid molecule.

* * * * *